United States Patent
Shinitzky et al.

(10) Patent No.: US 7,070,760 B1
(45) Date of Patent: Jul. 4, 2006

(54) SKIN TEST FOR SCHIZOPHRENIA

(75) Inventors: Meir Shinitzky, Kfar Shmaryahu (IL); Michael Deckmann, Guebwiller (FR)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/555,964

(22) PCT Filed: Dec. 7, 1998

(86) PCT No.: PCT/IL98/00592

§ 371 (c)(1), (2), (4) Date: Sep. 8, 2000

(87) PCT Pub. No.: WO99/30163

PCT Pub. Date: Jun. 17, 1999

(30) Foreign Application Priority Data

Dec. 7, 1997 (IL) .................................... 122490

(51) Int. Cl.
- *A61K 49/14* (2006.01)
- *G01N 33/53* (2006.01)
- *G01N 33/555* (2006.01)
- *G01N 33/567* (2006.01)

(52) U.S. Cl. .................. 424/9.1; 424/9.8; 435/7.2; 435/7.21; 435/7.24; 436/811

(58) Field of Classification Search ................ 435/7.2, 435/7.21, 7.24; 436/811; 424/9.1, 9.2
See application file for complete search history.

(56) References Cited

U.S. PATENT DOCUMENTS 5,429,947 A * 7/1995 Merril et al.

FOREIGN PATENT DOCUMENTS

WO 97/13152 4/1997

OTHER PUBLICATIONS

Kessler et al., Number of Platelet Dense Granules Varies with Age, Schizophrenia, and Dementia, Nov.-Dec. 1995, Demenita 6(6): 330-3.*
Stryer et al, in Biochemistry, Third edition, W H Freeman Company, New York, pp. 31-33, 1998.*
Jankovic et al, J Immunol 135(2 suppl): 583s-587s, Aug. 1985.*
Ovary et al, Adv Biol Skin 11: 103-21, 1971.*
Deckmann et al, Ital. J Psych Behav Sci 6: 29-34, 1996.*
"The Arthus Reaction and Delayed Hypersensitivity Reaction To Neurospecific Proteins s-100 and 10-40-4 In Schizophrinic Patients", *Biological Abstracts*, Abstract No. 24088, XP-002100216.

* cited by examiner

*Primary Examiner*—Christina Chan
*Assistant Examiner*—Phuong N Huynh
(74) *Attorney, Agent, or Firm*—Nath & Associates PLLC

(57) ABSTRACT

A diagnostic method for assaying schizophrenia in a subject is provided wherein a preparation comprising platelet derived proteins or fractions thereof having a pI above about 6.5 is injected into a subject and the occurrence of delayed type hypersensitivity (DTH) reaction at the site of the injection is determined. A positive DTH reaction indicates that the tested subject has a high likelihood of being schizophrenic. The protein preparation used in the diagnostic method is also provided as well as a method for its preparation and a kit for use in the diagnosis of schizophrenia using the above method.

4 Claims, 1 Drawing Sheet

SKIN TEST FOR SCHIZOPHRENIA

This application is a 371 of PCT/IL98/00592, filed Dec. 7, 1998, and claims the benefit of foreign application IL 122490, filed Dec. 7, 1997.

FIELD OF THE INVENTION

The present invention relates to diagnostic tests, and more specifically to diagnostic tests for psychiatric diseases.

LIST OF REFERENCES

The following is a list of references which is considered to be pertinent for the purpose of understanding the background of the invention:
1. Nyland, H., Naess, A. and Lundre, H.: *Lymphocyte subpopulations in peripheral blood from schizophrenic patients. Acta Psychiat. Scand.*, 1980; 61; 313–318.
2. Hirata-Hibi, M., Higashi, S., Tachibana, T. and Watanabe N., *Stimulated lymphocytes in schizophrenia Arch. Gen. Psychiat.* 1982; 39; 82–87.
3. Coeffey, C. E., Sullivan, J. L. and Rice, R. R., *T lymphoyctes in schizophrenia. Biol. Psychiatry* 1983; 18; 113–119.
4. Kolyaskina, G. I. *Blood lymphocytes in schizophrenia—immunological and virological aspects. Adv. Biol. Psychiat.* 1983; 12; 142–149.
5. Bessler, H., Eviatar J., Meshulan. M., Tyano. S., Djaldetti, M. and Sirota P. *Theophyllin-sensitive T-lymphocyte subpopulation in schizophrenic patients. Biol. Psychiatr.* 1987; 22; 1025–1029.
6. Muller, N., Ackenheil, M., Eckstein, R., Hofschuster, E. and Mempel, W. *Reduced suppressor cell function in psychiatric patients. Ann. N.Y. Acad. Sci.* 1987; 396; 686–690.
7. Mihalovic, L. J. and Jankovic B. D. *Effects of intraventricularly injected anti-caudatus antibody on the electrical activity of the cat brain. Nature* 1961; 192; 665.
8. Rapport, M. M., Karplak, S. E. and Mahadik, S. P. *Biological activities of antibodies injected into the brain. Fed. Proc.* 1979; 38; 2391.
9. Vartanian, M. E. Doyskina, G. S. Lozovsky, D. V., Burbaera, G. S. and Ignaton, S. A. *Aspects of humoral and cellular immunity in schizophrenia. In: Birth Defects. Original Article Series* D. Bergsma and A. Goldstein, eds. vol 14; 339–364; Alan R. Liss; New York, N.Y.; 1978.
10. Rotman, A. *Blood platelets in psychopharmacological research. Prog. Neuropsycopharmacol.* 1983; 6; 135–151.
11. Pletscher, A. *Biological Psychiatry*, Gea Racagni, ed; Elsevier Science Publisher; 1991; 2, 354–356.
12. Shinitzky, M., Deckmann, M., Kessler, A., Sirota, P., Rabbs, A. and Elizur, A., *Platelet autoantibodies in dementia and schizophrenia—possible implications for mental disorders. Ann. N.Y. Acad Sci.* 1991; 621; 205–217.
13. Kessler, A. and Shinitzky, M., *Platelets from schizophrenic patients bear autoantiboies that inhibit dopamine uptake. Psychobiology* 1993; 21; 229–306.
14. PCT Patent Application WO 95/23970.
15. Shinitzky, M. et al., WO 97/13152.
16. Deckmann et al., *Italian Journal of Psychiatry and Behavioural Sciences,* 6:29–34, 1996.

The above references will be acknowledged in the text below by indicating their number from the above list shown in brackets.

BACKGROUND OF THE INVENTION

Schizophrenia is a syndrome which encompasses a variety of symptoms including paranoia, auditory hallucination, delusions, catatonia, bizarre behavior and emotional withdrawal. Schizophrenia affects about 1% of the total population. Its economical and social burden on society is enormous since onset occurs in youth thus requiring patients to be under medical and psychiatric supervision for most of their lives. Schizophrenia is therefore one of the most costly diseases in the industrialized world.

Since the biochemical basis of schizophrenia has not yet been elucidated, diagnosis today is still based solely upon psychiatric evaluation. Furthermore, no therapy is currently available for schizophrenia although the symptoms may be ameliorated by neuroleptic drugs.

Many reports have implicated the immune system in the etiology and course of several mental disorders. Serum antibodies which cross-react with brain antigens have been found in the blood of schizophrenic patients[1–6], thus indicating that schizophrenia is also an autoimmune disease[7–9]. Furthermore, platelets have been used as a model for neuronal tissue[10,11] and elevated levels of autoantibodies to platelets have been detected in schizophrenic and demented patients, but not in patients suffering from manic-depressive disorder, depression, personality disorders or schizoaffective disorders[12–14]. An assay for the diagnosis of multi-infarct dementia and dementia of the Alzheimer type was described based on detection of a high level of a platelet associated antibody[15].

A cellular response against autologous platelets was also demonstrated in schizophrenia patients who showed a delayed type hypersensitivity (DTH) reaction when injected with platelets collected from their own blood[16].

It is therefore the object of the present invention to provide a test for the diagnosis of schizophrenia in a subject.

SUMMARY OF THE INVENTION

A novel finding in accordance with the invention is that schizophrenic patients exhibit a reaction which displays characteristics of a typical delayed-type hypersensitivity reaction when injected with a specific, novel fraction of platelet proteins. This novel fraction is referred to herein as "Pool 2 proteins". The Pool 2 proteins, which constitute an aspect of the invention, are characterized by having an isolectric point (pI) which is above about 6.5 and preferably within the range of about 6.5 to about 9.5. When injected with Pool 2 proteins, schizophrenic patients show such a delayed-type hypersensitivity (DTH) reaction.

It is to be noted that although the reaction of the patients to the Pool 2 proteins is referred to above and below as a DTH reaction, there may be cases in which the time profile of the reaction of the patient to the Pool 2 proteins will be different than the time profile of a typical DTH reaction.

The present invention thus provides a protein preparation (hereinafter "Pool 2 proteins") comprising platelet derived proteins or fractiions thereof having an isoelectric point (pI) above about 6.5 and preferably within the range of above 6.5 to about 9.5, said preparation capable of eliciting a DTH reaction in a schizophrenic individual upon injection thereof to the individual.

The present invention further provides a diagnostic method for assaying schizophrenia in a subject comprising:
(a) obtaining a preparation comprising, as an active component, platelet derived proteins or fractions thereof having an isoleectric point (pI) above about 6.5 and preferably within the range of about 6.5 to about 9.5 ("pool 2 proteins");

(b) injecting said protein preparation into a subject; and (c) examining the subject for the occurrence of a delayed type hypersensitivity reaction at the site of the injection, a positive result being a reaction above that which is observed in non-schizophrenic sujects, indicating that the subject has a high likelihood of being schizophrenic.

In accordance with the invention it was also surprisingly found that the Pool 2 proteins may be either prepared from autologous platelets of the individual to be tested or, alternatively, from a pool of hetrologous platelets which were obtained from a number of individuals other than the tested subject. It was also surprisingly found that, in most cases, the DTH reaction in a schizophrenic patient is substantially higher when the individual is injected with such Pool 2 proteins obtained from a pool of heterologous platelets as compared to a lower DTH reaction in the same tested individual injected with Pool 2 proteins prepared from his own autologous platelets. This finding provides the advantage of preparing a pool 2 protein preparation which may then either be used immediately or alternatively, be stored at appropriate conditions (e.g. refrigeration) and used for various periods of time to diagnose schizophrenia in a large number of individuals. This obviates the need to repeatedly obtain a blood sample comprising platelets from the tested individual immediately prior to carrying out the diagnostic assay of the invention.

Thus, by a preferred embodiment, the present invention further provides a method for the preparation of a reagent for use in diagnosis of schizophrenia, comprising:

(a) obtaining blood samples from a number of individuals preparing a pool from said samples and collecting platelets therefrom; (b) preparing a protein fraction from said platelet preparation comprising proteins or fractions thereof having a pI of above about 6.5, preferably within the range of about 6.5 to about 9.5.

The Pool 2 proteins prepared from heterologous individuals may either be prepared from a number of individuals suffering from schizophrenia or, alternatively, also from a mixture of blood samples obtained from schizophrenic patients as well as healthy individuals.

The present invention yet further provides a diagnostic method for assaying schizophrenia in a subject comprising:

(a) obtaining a blood sample from a number of schizophrenic and/or non schizophrenic individuals other than the tested subject and collecting platelets therefrom;

(b) preparing a protein fraction from said platelet separation comprising proteins or fractions thereof having a pI of above about 6.5, preferably within the range of above 6.5 to about 9.5;

(c) injecting said protein preparation into a subject; and (d) examining the subject for the occurrence of a delayed type hypersensitivity reaction at the site of the injection, a positive result being a reaction above that which is observed in non-schizophrenic subjects, indicating that the subject has a high likelihood of ein schizophrenic.

By a preferred embodiment, a method for diagnosis of schizophrenia in an individual is provided as above wherein the protein fraction collected in stage (b) is then stored as appropriate conditions for repetitive use as described in stages (c) and (d) above at later priods of time for a number of tested individuals.

Although, as explained above, there is an advantage in preparing a pool of Pool 2 proteins from a number of individuals other than the individual to be tested, in accordance with the diagnostic method of the invention, it is also possible to use Pool 2 preparation prepared from autologous platelets of the individual to be tested.

The present invention thus provides a diagnostic method for assaying schizophrenia in a subject comprising:

(a) obtaining a blood sample from an individual and collecting platelets therefrom;

(b) collecting proteins or fractions hereof from said platelet sample, said proteins or fractions having a pI of above about 6.5, preferbly within the range of about 6.5 to about 9.5;

(c) injecting said collected protein or fractions thereof to the tested individual; and (d) examining the subject for the occurrence of delayed type hypersensitivity reaction at the site of the injection, a positive result being a reaction above that which is observed in non-schizophrenic subjects, indicating that the subject has a high likelihood of being schizophrenic.

Typically, the Pool 2 proteins will be collected by subjecting the collected platelet proteins to isoelectric focusing wherein the proteins haveing a pI of above about 6.5, preferably within the range of 6.5 to 9.5 are collected by methods known in the art.

However, in accordance with the invention it has also been found that the Pool 2 protein preparation may also be prepared by methods which do not include isoelectric focusing such as, for example, by extracting the proteins from the platelet sample using for example a detergent, such extraction resulting in Pool 2 proteins having the desired pI values and capable of eliciting a DTH reaction in a schizophrenic patient.

If desired, the Pool 2 protein preparation obtained by any one of the methods mentioned above may be subject to further fractionation steps, e.g. by thin layer chromatography, by high pressure liquid chromatography or by many other purification fractionation methods known, per se. Fractions thus obtained can each then be tested for activity, namely for its ability to cause the DTH reaction in schizophrenic patients. Such purified fractions, as well as individual proteins, polypeptides or peptides among the Pool 2 proteins which are active in eliciting he DTH reaction in schizophrenic patients, are also an aspect of the invention.

The Pool 2 protein preparation prepared in accordance with the invention and used in the diagnostic methods of the invention include proteins purified from the Pool 2 proteins, polypeptides or peptides comprising sequences of such proteins, fractions thereof, as well as proteins, polypeptides or peptides obtained by synthesis or by genetic engineering having a sequence identical to that of the proteins of the Pool 2 proteins.

In accordance with the invention, Pool 2 proteins used in the diagnostic assay of the invention are such which are capable of eliciting DTH activity in an injected individual, the DTH activity being tested by the test known in the art.

In short, the Pool 2 proteins are intradermally injected into the tested individual at the forearm or thigh and the reaction at the injection site is evaluated after 24, 48 and 72 hours by measuring the reaction diameter around the induration. As mentioned above, there may be cases in which the time profile of the reaction will differ from the typical time profile of a DTH reaction.

The present invention further provides a kit for use in diagnosis of schizophrenia, comprising said Pool 2 proteins, active protein fractions obtained therefrom, or individual active proteins or peptides, derived from said Pool 2 proteins. Preferably, such proteins are provided in either injectable form or in a form suitable for preparing an injectable formulation, e.g. a lyophilysate. Typically, the kit will be provided with instructions for use or a chart or pictures for guidance of the manner of scoring the results.

Figure 1:
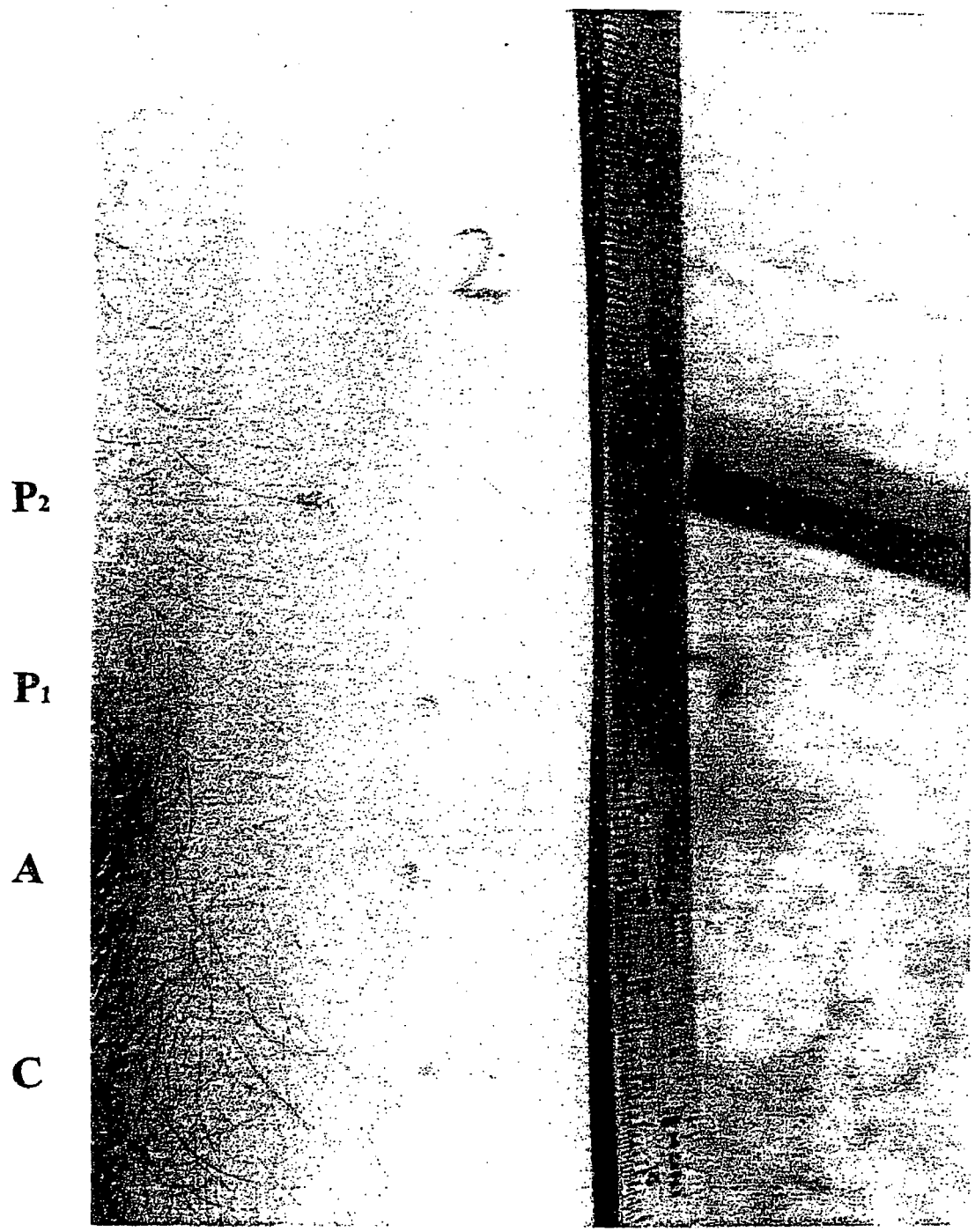
FIG. 1 shows the reaction on the forearm of a schizophrenic patient which was injected with the following preparations:
  i. Pool 2 proteins (marked as P2)
  ii. Pool 1 proteins (marked as P1)
  iii. Autologous platelets (marked A)
  iv. PBS (marked as C=control).

The invention will now be illustrated in the following examples, which are annexed to the above drawings.

EXAMPLES

A study on the reaction of a subject to an injection of platelets collected from his or her own blood or an injection of Pool 2 proteins was carried out in Israel at The Hospital for Mental Health in Sha'ar Menashe, The Geriatric Hospital in Pardes Hana and at the Weizmann Institute of Science.

Example 1

Injection of Autologous Proteins

1. Preparation of Platelets
10 ml venous blood was collected from a subject and centrifuged for 20 mins. at 20° C. and 150 g. The supernatant containing platelets was collected and centrifuged three times for 10 min. at 20° C. and 2000 g and the platelets resuspended in phosphate buffered saline (PBS) containing 5 mM EDTA. After the last washing, the platelets were resuspended in sterile PBS at a final concentration of $2 \times 10^8$ platelets/ml.

2. Autologous Skin Test and Measurement of Delayed Type Hypersensitivity (DTH) Reaction
0.1 ml of the platelet suspension obtained as above from a particular subject was injected intradermally back into the forearm of the same subject. A second injection of 0.1 ml PBS spaced about 10 cm from the point of sample injection served as a control.

DTH reaction at the injection sites was measured in accordance with methods known in the art (Skornik, Y., et al., *Cancer Immunol. Immunother.* 11:93–96, 1981).

Results
The tests were carried out for groups subject:
a) 18 healthy subjects under the age of 65.
b) 10 healthy subjects above the age of 65.
c) 41 schizophrenic pateints.
d) 21 demented patients.

The results of this test are shown in the following Table 1.

TABLE 1

Autologous (Self—Self) Skin Reaction Against Platelets in Humans for the Detection of Schizophrenia
Summary of a Multi-Center Study

| Schizophrenic Persons n = 41 | | Non-schizophrenic Persons n = 49 | |
|---|---|---|---|
| Skin Reaction positive: | 25 | Skin Reaction positive: | 0 |
| Skin Reaction borderline: | 13 | Skin Reaction borderline: | 1 |
| Skin Reaction negative: | 3 | Skin Reaction negative: | 48 |
| Total Sensitivity: | 92% | Total Specificity: | 98% |

As can be seen, 38 out of the 41 schizophrenic patients showed a DTH reaction, while only one healthy individual under the age of 65 out of the 18 which were tested, reacted positively. Positive reactions were not observed in 10 healthy individuals over the age of 65, as well as in 21 demented patients. Sensitivity of this test is thus 92% and the specificity is 98%.

As seen in the Table, while almost all of the tested schizophrenic patients showed a DTH reaction to the Pool 2 proteins prepared from their autologous platelets, only one healthy individual had a positive DTH reaction. Thus, the diagnostic assay of the invention showed a very high sensitivity and specificity for the diagnosis of schizophrenia in a tested individual.

Example 2

Preparation of Pool 1 and Pool 2 Proteins

Methods
Platelet suspension containing about 20 gr total protein was obtained as in Example 1, and the platelets solubilized with 40 ml of a solution containing 0.5% of the detergents NP-40 and Triton-X-100 for 5 mins. at room temperature with gentle shaking. The solution was then centrifuged at 4000 g for 15 mins. at 20° C. The supernatant was collected, and the pellet was subjected to two further extractions with 10 ml 0.1% Triton-X-100. The three supernatants were combined and Bio-Lyte Ampholyte™ 3/10 (40%) of BioRad was added to a final concentration of 1%. The solubilized proteins were subjected to isoelectric focusing. 60 ml of sample was applied to the Rotofor™ system of BioRad, using 0.1 M phosphoric acid as anode solution, and 0.1 M NaOH as cathode solution. The isoelectric focusing was performed for about 4 hours at 10° C. using 10 Watt constant power until the current remained constant for 30 mins. Proteins were divided into two separate groups in accordance with their pI; proteins having a pI in the range of 2–6.5 are referred to as Pool 1 proteins while proteins having a pI in the range of 6.5–9.5 are referred to as Pool 2 proteins. Pool 1 and Pool 2 proteins were harvested separately and diluted 1:50 with PBS.

Example 3

Injection of Pool 1 and Pool 2 Proteins

Method
The following four preparations were injected intradermally into the forearm of a schizophrenic patient:
  i. Pool 2 proteins (marked as P2)
  ii. Pool 1 proteins (marked as P1)

iii. Autologous platelets (marked A)
iv. PBS.

0.1 ml of each above preparation were injected and the preparations were injected at four different injection sites spaced about 10 cm from each other. The skin reaction at each injection site was monitored 24 h, 48 h and 72 h after injection.

Results

The results are seen in FIG. 1 where (i) is the highest injection site on the arm and (iv) is the lowest.

As seen in the FIGURE, a DTH response measured as explained above, was observed in a schizophrenic patient at the site of injection of Pool 2 proteins and no DTH reaction was seen at the site of P1 injection. Furthermore, the DTH reaction at the P2 site of injection was substantially enhanced as compared to the DTH reaction seen at the site of injection of the autologous platelets. Thus, it is, in most cases, preferred to use a P2 protein preparation obtained from a pool of blood samples obtained from several heterlogous individuals in the diagnostic assay of the invention.

The invention claimed is:

1. A method for the preparation of a reagent for use in diagnosis of schizophrenia in an individual by detecting a DTH reaction in said individual following injection of said reagent to the individual, comprising
   a) obtaining blood samples from a number of individuals, preparing a pool from said samples and collecting platelets therefrom;
   b) preparing a protein fraction from said platelet preparation comprising proteins or fractions thereof, wherein the pI of said proteins or fractions thereof is about 6.5 to about 9.5;
   c) injecting the platelet preparation of step b) into a subject; and
   d) detecting the occurrence of a DTH reaction at the site of injection, wherein a positive result is a reaction above that observed in a non-schizophrenic subject under similar conditions, and it indicates that the subject has a high likelihood of being schizophrenic.

2. A diagnostic method for determining schizophrenia in a subject comprising
   a) obtaining a preparation comprising platelet derived proteins or fractions thereof, wherein the pI of said proteins or fractions thereof is about 6.5 to about 9.5;
   b) injecting said preparation into a subject; and
   c) examining the subject for the occurrence of delayed type hypersensitivity reaction at the site of the injection, a positive result being a reaction above that which is observed in non-schizophrenic subjects, indicating that the subject has a high likelihood of being schizophrenic.

3. A diagnostic method for determining schizophrenia in a subject comprising:
   (a) obtaining a blood sample from a number of schizophrenic or non schizophrenic individuals other than the tested subject and collecting platelets therefrom;
   (b) preparing a protein fraction from said platelet separation comprising proteins or fractions thereof, wherein the pI of said proteins or fractions thereof is about 6.5 to about 9.5;
   (c) injecting said protein preparation into a subject; and
   (d) examining the subject for the occurrence of a delayed type hypersensitivity reaction at the site of the injection, a positive result being a reaction above that which is observed in non-schizophrenic subjects, indicating that the subject has a high likelihood of being schizophrenic.

4. A diagnostic method for determining schizophrenia in a subject comprising:
   a) obtaining a blood sample from an individual and collecting platelets therefrom;
   b) collecting proteins or fractions thereof from said platelet sample, wherein the pI of said proteins or fractions is about 6.5 to about 9.5;
   c) injecting said collected proteins or fractions thereof to the tested individual; and
   d) examining the subject for the occurrence of delayed type hypersensitivity reaction at the site of the injection, a positive result being a reaction above that which is observed in non-schizophrenic subjects, indicating that the subject has a high likelihood of being schizophrenic.

* * * * *